(12) United States Patent
Cooper et al.

(10) Patent No.: US 9,513,473 B2
(45) Date of Patent: Dec. 6, 2016

(54) FLUORESCENCE MICROSCOPES WITH POLYCHROIC MIRROR CHANGERS

(75) Inventors: Jeremy R. Cooper, Issaquah, WA (US); Justin Kyle Curts, Issaquah, WA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 83 days.

(21) Appl. No.: 14/234,459

(22) PCT Filed: Jul. 10, 2012

(86) PCT No.: PCT/SE2012/050821
§ 371 (c)(1),
(2), (4) Date: Jan. 23, 2014

(87) PCT Pub. No.: WO2013/015734
PCT Pub. Date: Jan. 31, 2013

(65) Prior Publication Data
US 2014/0177045 A1      Jun. 26, 2014

Related U.S. Application Data

(60) Provisional application No. 61/511,094, filed on Jul. 24, 2011.

(51) Int. Cl.
  *G02B 21/06*  (2006.01)
  *G01N 21/64*  (2006.01)
  *G02B 21/16*  (2006.01)

(52) U.S. Cl.
  CPC ............ *G02B 21/06* (2013.01); *G01N 21/6458* (2013.01); *G02B 21/16* (2013.01); *G01N 2021/6419* (2013.01); *G01N 2021/6421* (2013.01); *G01N 2021/6423* (2013.01)

(58) Field of Classification Search
  CPC .. G02B 21/06; G02B 21/16; G01N 21/6458; G01N 2021/6419; G01N 2021/6423

USPC ......................... 359/388, 656–661, 850, 838
See application file for complete search history.

(56) References Cited

U.S. PATENT DOCUMENTS 6,222,671 B1    4/2001  Ogihara
6,624,930 B1    9/2003  Danner et al.
(Continued)

FOREIGN PATENT DOCUMENTS

WO        02/41064 A1    5/2002

OTHER PUBLICATIONS

EP Search Report for EP Application No. 12 81 8418 mailed Jan. 21, 2015 (3 pages).

*Primary Examiner* — Bumsuk Won
*Assistant Examiner* — Grant Gagnon
(74) *Attorney, Agent, or Firm* — Sutherland Asbill & Brennan LLP (57) ABSTRACT

Fluorescence microscopy systems with polychroic mirror changers are described. In one aspect, a polychroic mirror changer includes a polychroic-mirror array. The array includes a plate with a planar surface and a number of holes formed in the plate. The array also includes polychroic mirrors attached to the planar surface of the plate such that each polychroic mirror covers one of the holes and the reflective surface of each polychroic mirror is adjacent to and aligned with the planar surface of the plate. Each polychroic mirror is partially exposed through a corresponding hole to reflect a different subset of excitation channels of a beam of excitation light input to the changer. The polychroic-mirror array can be mounted in the changer so that when a different subset of excitation channels is selected to illuminate a specimen, the plate is moved within a single plane of motion.

19 Claims, 10 Drawing Sheets

(56) References Cited

U.S. PATENT DOCUMENTS

| | | | |
|---|---|---|---|
| 2003/0151742 A1* | 8/2003 | Silvermintz et al. | 356/318 |
| 2004/0246477 A1* | 12/2004 | Moon et al. | 356/300 |
| 2007/0177257 A1 | 8/2007 | Lauer | |
| 2008/0100911 A1* | 5/2008 | Tafas et al. | 359/385 |
| 2010/0302632 A1* | 12/2010 | Luttenberger | 359/390 |
| 2011/0002530 A1* | 1/2011 | Zhuang et al. | 382/154 |
| 2011/0096393 A1 | 4/2011 | Araki | |
| 2011/0102888 A1* | 5/2011 | Honda et al. | 359/385 |

\* cited by examiner

FLUORESCENCE MICROSCOPES WITH POLYCHROIC MIRROR CHANGERS

CROSS-REFERENCE TO A RELATED APPLICATION

This application is a filing under 35 U.S.C. 371 of international application number PCT/SE2012/050821, filed Jul. 10, 2012, published on Jan. 31, 2013 as WO 2013/015734, which claims the benefit of Provisional Application No. 61/511,094; filed Jul. 24, 2011.

TECHNICAL FIELD

This disclosure relates to fluorescence microscopy and, in particular, to fluorescence microscopes.

BACKGROUND

Fluorescence microscopes commonly utilize multiple polychroic mirrors attached to a polychroic changer in order to excite a number of different fluorescent emission channels that can be separately imaged. However, aligning the system for multiple polychroic mirrors remains a challenge. In particular, replacing one polychroic mirror located in an excitation beam path with another is difficult to achieve with a high degree of alignment precision and repeatability. In addition, co-alignment of the multiple polychroic mirrors is very difficult to achieve.

Prior approaches include using polychroic mirrors that are mounted to angled surfaces of turret systems. Each angled position of the turret has a different polychroic mirror. A conventional turret has repeatability problems because there are typically multiple parts that index the polychroic mirror position with respect to one another as well as with high respect to the microscope. This makes it nearly impossible to guarantee with precision that two or more polychroic mirrors are co-aligned. It is possible to add mechanical adjustment controls to provide the necessary degrees of freedom to co-align multiple polychroic mirrors. However, these additional mechanical adjustment controls increase the costs and complexity of a microscope considerably, as well as further reducing long term alignment repeatability. For instance, adding parts associated with an adjustment mechanism to a polychroic mirror changer results in changes in positions of the optical components over time. For these reasons, fluorescent microscope manufactures and engineers continue to seek reliable systems for changing polychroic mirrors.

SUMMARY

Fluorescence microscopy systems with polychroic mirror changers are described. In one aspect, a polychroic mirror changer includes a polychroic-mirror array. The array includes a plate with a planar surface and a number of holes formed in the plate. The array also includes polychroic mirrors attached to the planar surface of the plate such that each polychroic mirror covers one of the holes and the reflective surface of each polychroic mirror is adjacent to and aligned with the planar surface of the plate. Each polychroic mirror is partially exposed through a corresponding hole to reflect a different subset of excitation channels of a beam of excitation light input to the changer. The polychroic-mirror array can be mounted in the changer so that when a different subset of excitation channels is selected to illuminate a specimen, the planar surface slides across at least three kinematic points of contact so that the array is moved within a single plane of motion.

DETAILED DESCRIPTION

Figure 1:
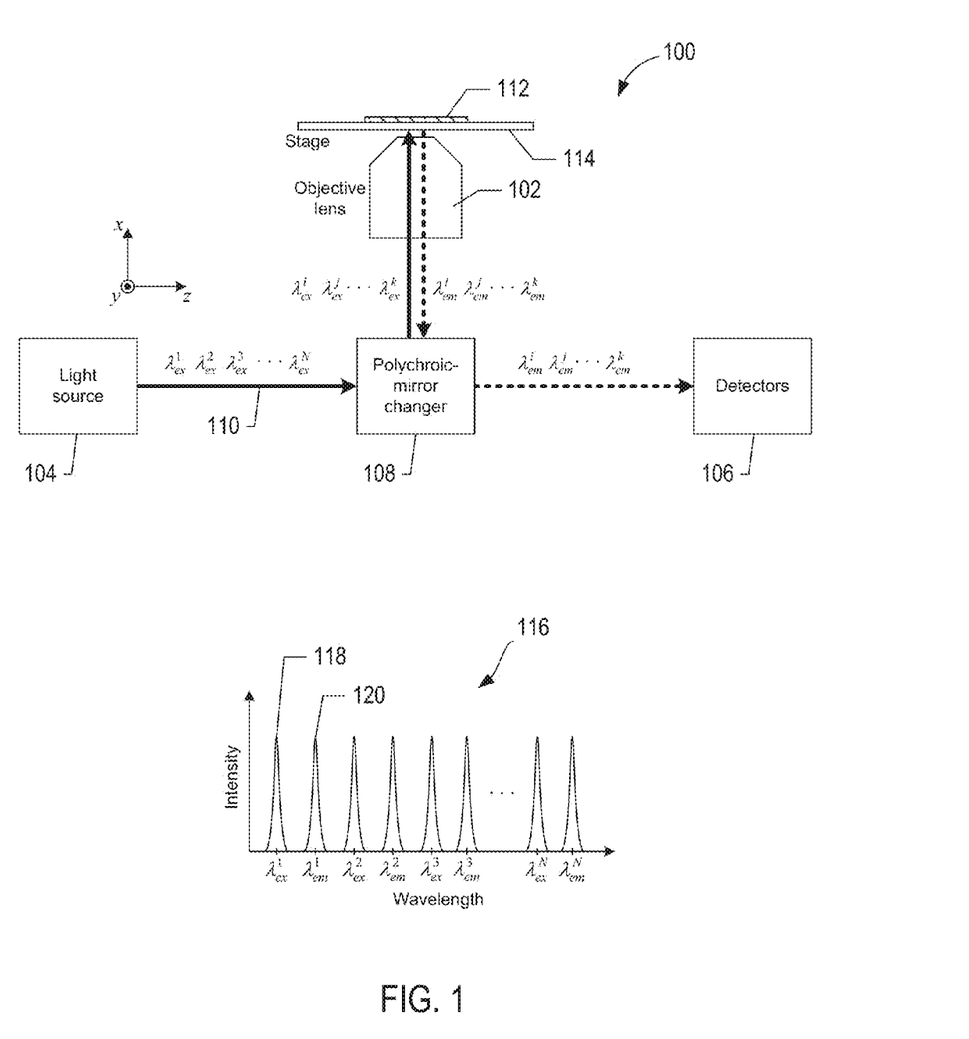
FIG. 1 shows an isometric view of an example microscopy instrument.

FIG. 1 shows a schematic representation of an example microscopy instrument 100. The instrument 100 includes an objective lens 102, a light source 104, detectors 106, and a polychroic-mirror changer 108. The light source 108 can generate a high-intensity beam of light 110 composed of N separate monochromatic excitation wavelengths denoted by $\lambda_{ex}^i$, where N is an integer and i is an integer index that ranges from 1 to N. A specimen disposed on a microscope slide 112 is supported by a stage 114. Components of the specimen are labeled with fluorescent probes. Each type of probe is designed to bind specifically to a particular component of the specimen, and each type of fluorophore is bound to a particular type of probe so that when the specimen is illuminated with the beam 110, each fluorophores emits light with different emission wavelength $\lambda_{em}^i$ in the visible and near-visible portion of the electromagnetic spectrum. In other words, each component of the specimen can be displayed with a different associated wavelength. In other words, the N excitation wavelengths excite emission from the N different types of fluorophores. FIG. 1 includes a plot 116 of intensity versus a range of wavelengths in the visible spectrum. Each curve of the plot 116 represents an intensity distribution over a very narrow range of wavelengths centered about a particular wavelength. For example, curve 118 represents a narrow range of excitation wavelengths centered about an excitation wavelength $\lambda_{ex}^1$ that excites a first type of fluorophore, and curve 120 represents a narrow range of emission wavelengths centered about an emission wavelength $\lambda_{em}^1$ emitted by the first fluorophore. When the emission wavelengths are in the visible portion of the electromagnetic spectrum, the components can be displayed in an image of the specimen with different colors. The N excitation wavelengths are called "excitation channels," and the N wavelengths of light emitted from the N types of fluorophores are called "emission channels."

As shown in the example of FIG. 1, the changer 108 receives the beam 110 and is operated to select a subset composed one or more of the excitation channels to pass through the objective lens 102 to illuminate the specimen. The corresponding emission channels are collected by the objective and directed by the changer to detectors 106. For example, the changer 108 is operated to select a subset of excitation channels $\lambda_{ex}^i, \lambda_{ex}^j, \ldots, \lambda_{ex}^k$ from the full set of excitations channels in the beam 110 pass through the objective lens 102 to illuminate the specimen. The corresponding fluorophores emit light in emission channels $\lambda_{em}^i, \lambda_{em}^j, \ldots, \lambda_{em}^k$, which are collected by the objective lens 102 and directed by the changer 108 to the detectors 106. The detectors 106 can be a photodetector array, CCD cameras, or CMOS cameras.

Figure 2:
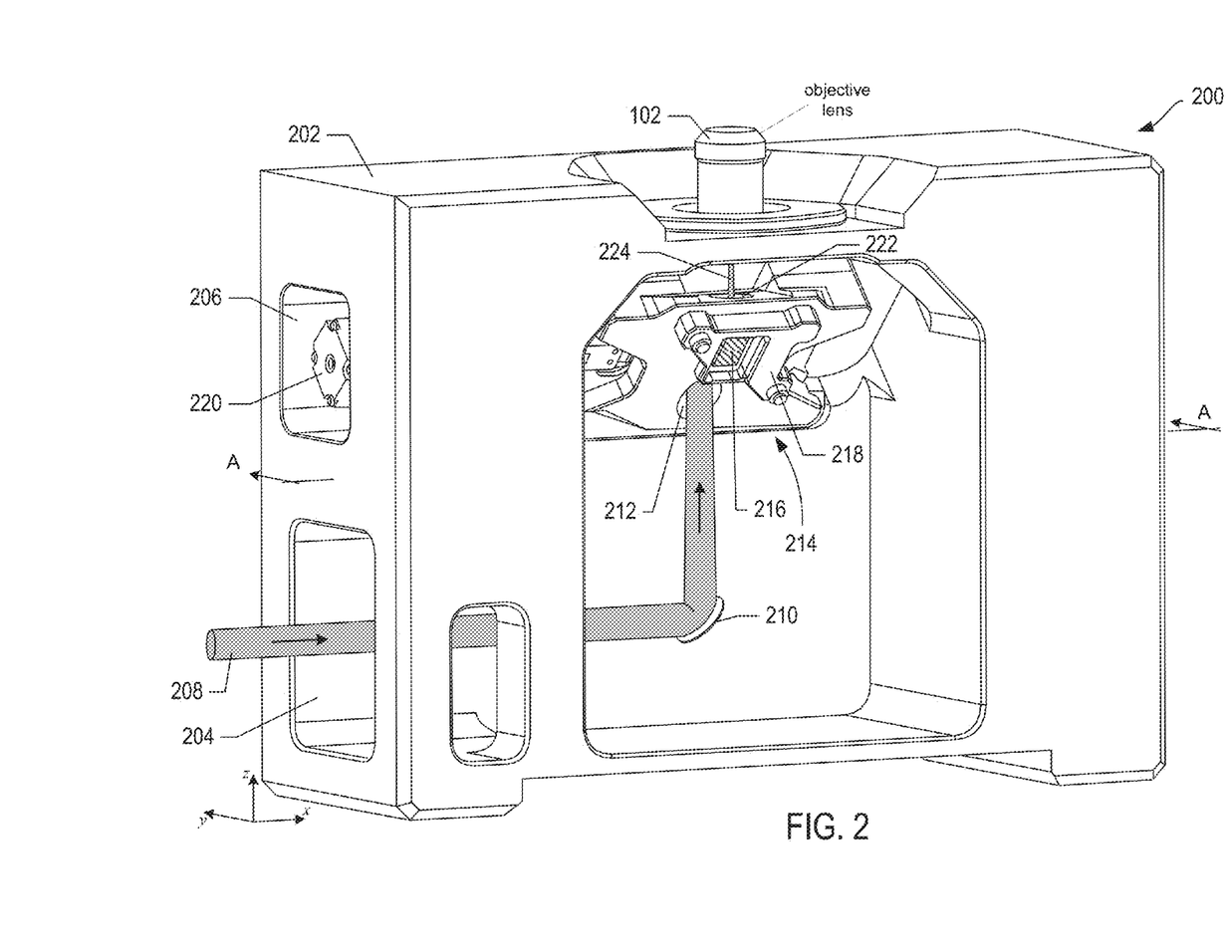
FIG. 2 shows an isometric view of an example polychroic-mirror changer of a modular imaging system.

FIG. 2 shows an isometric view of an example implementation of a polychroic-mirror changer 200. The changer 200 includes a housing 202 with a first opening 204 and a second opening 206 located above the first opening 204. A beam of excitation light 208 produced by the light source enters the housing 202 through the first opening 204 and is reflected from a mirror 210 into an opening 212 of an excitation-channel selector 214. The selector 214 includes a mirror 216 and a mirror support 218 that fixes the position of the mirror 216 and includes a motor 220 disposed within the second opening 206. The selector 214 selects one channel or a subset of the channels that are output through an opening 222 as a beam 224 that enters the objective lens to illuminate a specimen disposed on the stage 104.

Figure 3:
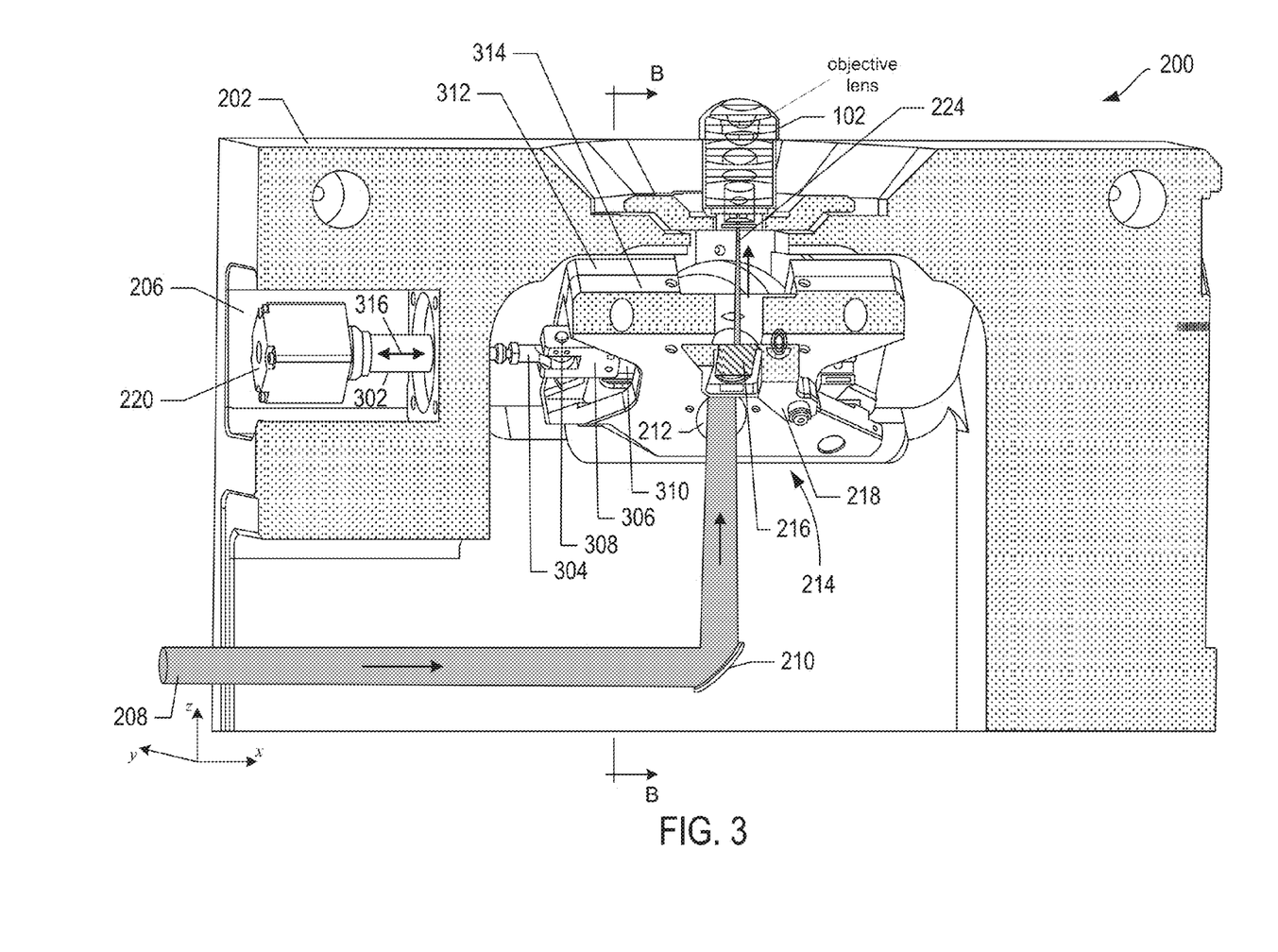
FIG. 3 shows a cross-sectional view along a line A-A, shown in FIG. 2, of the polychroic-mirror changer.

FIG. 3 shows a cross-sectional view along a line A-A, shown in FIG. 2, of the polychroic-mirror changer 200 that reveals components of the excitation-channel selector 214. As shown in FIG. 3, the selector 214 includes a shaft 302 attached at one end to the motor 220 and at the opposite end to a spherical rod end 304. The spherical rod end 304 fits within a U-shaped end of a yolk 306 and is attached to the yolk 306 via a clevis pin 308. The selector 214 also includes a polychroic-mirror array 310 located between a first support 312 attached to the housing 202 and a second support 314 attached to the first support 312. The polychroic mirror array 310 is attached to the yolk 306 opposite the U-shaped end. The motor 220 can be a stepper motor or a linear actuator that moves the shaft 302 back and forth at regular incremental distances, as indicated by directional arrow 316. As a result, the polychroic mirror array 310 is also moved by the same distances within an opening (not shown) between the first and second supports 312 and 314.

Figure 4A:
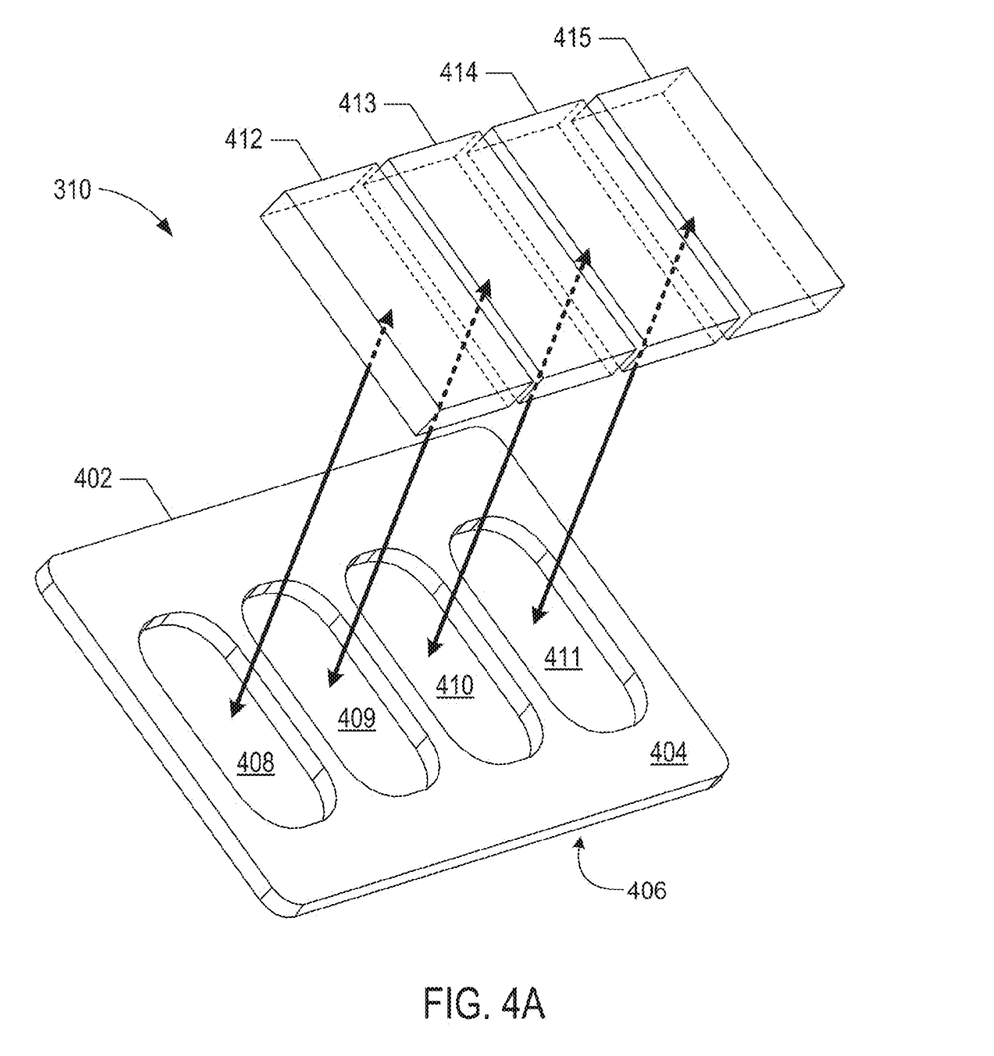
FIG. 4A shows an exploded isometric view of an example polychroic-mirror array with a one-dimensional array of polychroic mirrors.
Figure 4B:
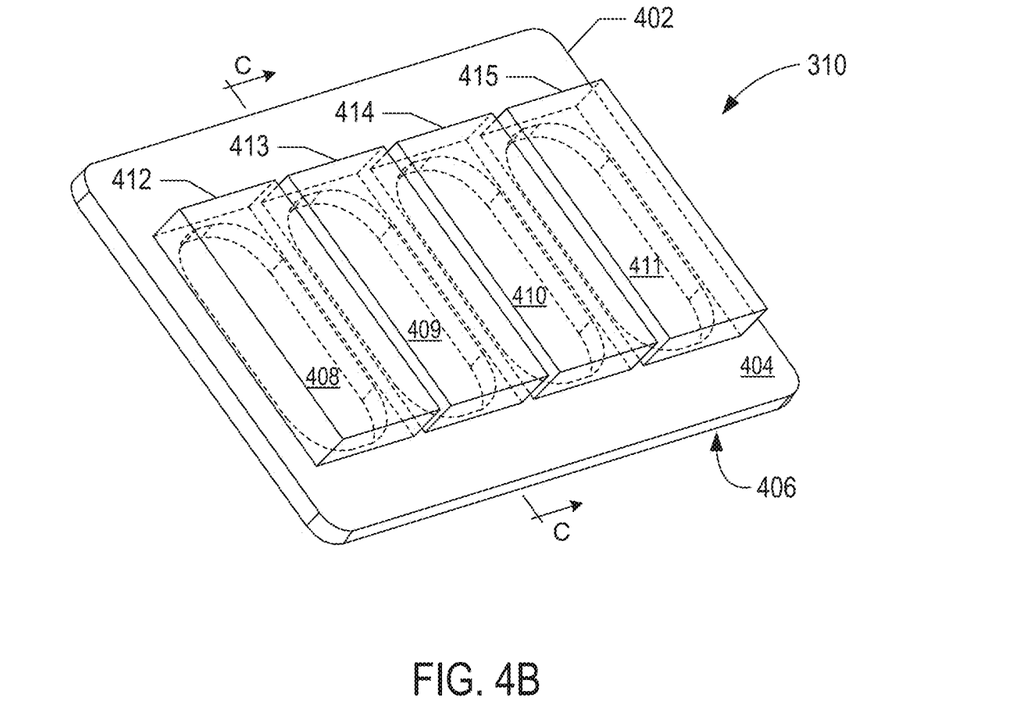
FIG. 4B shows an isometric view of the polychroic-mirror array plate.
Figure 4C:
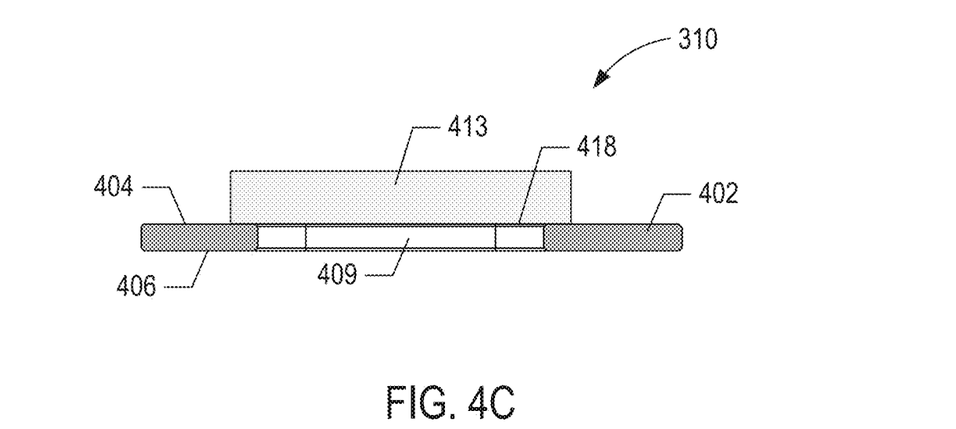
FIG. 4C shows a cross-sectional view of the polychroic-mirror array along a line C-C shown in FIG. 4B.

FIG. 4A shows an exploded isometric view of an example polychroic-mirror array 310. The array 310 includes a flat, uniformly thick, rectangular-shaped plate 402 composed of steel, carbide, or another suitable wear resistant material. The plate 402 has a planar first surface 404 and a planar second surface 406 that is parallel to and opposite the first surface 404. In other embodiments, the plate 402 can be composed of a rigid material and the first surface 404 can be coated or implanted with a highly polished wear resistant material, such as a ceramic coating. In the example of FIG. 4A, the plate 402 includes a one-dimensional arrangement of four regularly spaced, elongated holes 408-411 and four corresponding polychroic mirrors 412-415 shown detached from the first surface. The reflective surfaces of the mirrors 412-415 are adjacent to and aligned with the first surface 404. FIG. 4B shows an isometric view of the plate 402 with the four polychroic mirrors 412-415 attached to the first surface 404 to form the array 310. The polychroic mirrors 412-415 are mounted with the reflective surfaces facing, or coplanar to, the first surface 404. As shown in FIG. 4B, each of the polychroic mirrors 412-415 covers one of the holes 408-411. FIG. 4C shows a cross-sectional view of the array 310 along a line C-C shown in FIG. 4B. The outer edges of the reflective surface 418 of the polychroic mirror 413 are attached to the first surface 404 using an adhesive, such as glue or an epoxy, exposing the rest of the reflective surface 418 through the hole 409. Each polychroic mirror reflects and transmits a different subset of channels of the beam 208 input to the excitation-channel selector 214, as described in greater detail below with reference to FIGS. 7 and 8.

Figure 5:
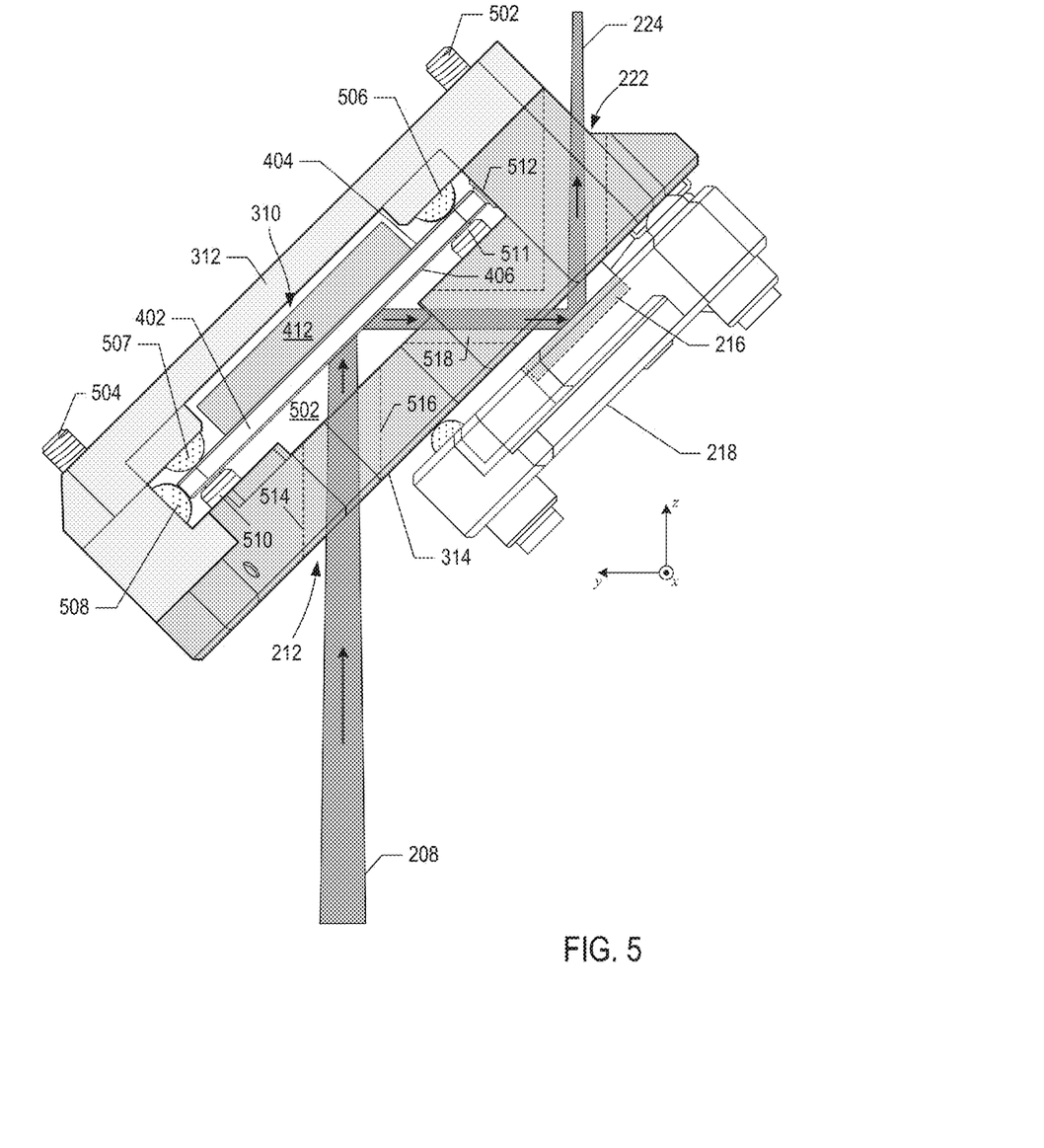
FIG. 5 shows a side view of supports for a polychroic-mirror array.

FIG. 5 shows a side view of the first and second supports 312 and 314 and the mirror support 218 attached to the second support 314. The first support 312 includes two screws 502 and 504 that attach the first support 312 to the housing 202 as shown in FIG. 3. This side view reveals that the first and second supports 312 and 314 have facing recesses that form an opening 502 into which the polychroic-mirror array 310 is placed. Hemispheres 506-508 represent exposed portions of kinematic balls that contact the plate 402. The kinematic balls 506 and 507 are partially embedded within sockets (not shown) of the first support 312 and make contact with the first surface 404. In other words, the kinematic balls 506 and 507 make contact with same surface 404 of the plate 402 to which the reflective surfaces of the polychroic mirrors are attached. The kinematic ball 508 is also embedded within the first support 314 and makes contact with the edge of the plate 402. The first support 312 includes at least one other kinematic ball (not shown) that makes contact with the first surface 404 and can be located behind the ball 506 or the ball 507. The second support 314 includes preloaded sliding elements 510-512 that force the plate 402 into contact with the kinematic balls 506-508. The elements 510 and 511 make contact with the second surface 406, and the element 512 makes contact with an edge of the plate 402. As the array 310 is moved back and forth in the opening 502 in the x-direction, the kinematic balls remain stationary as the array 310 slides smoothly back and forth within the opening 502. Dashed lines, such as dashed lines 514 and 516, identify openings in the second support 314 that allow unobstructed transmission of the beam 208. For example, dashed lines 514 and 516 identify the opening 212, shown in FIG. 2, through which the beam 208 passes to interact with the array 310 positioned above the opening 212. The polychroic mirror reflects selected channels of the beam 208 to pass through an opening 518, which are reflected from the mirror 216 of the mirror support 218 to pass through the opening 222 and into the objective lens as the beam 224.

Figure 6:
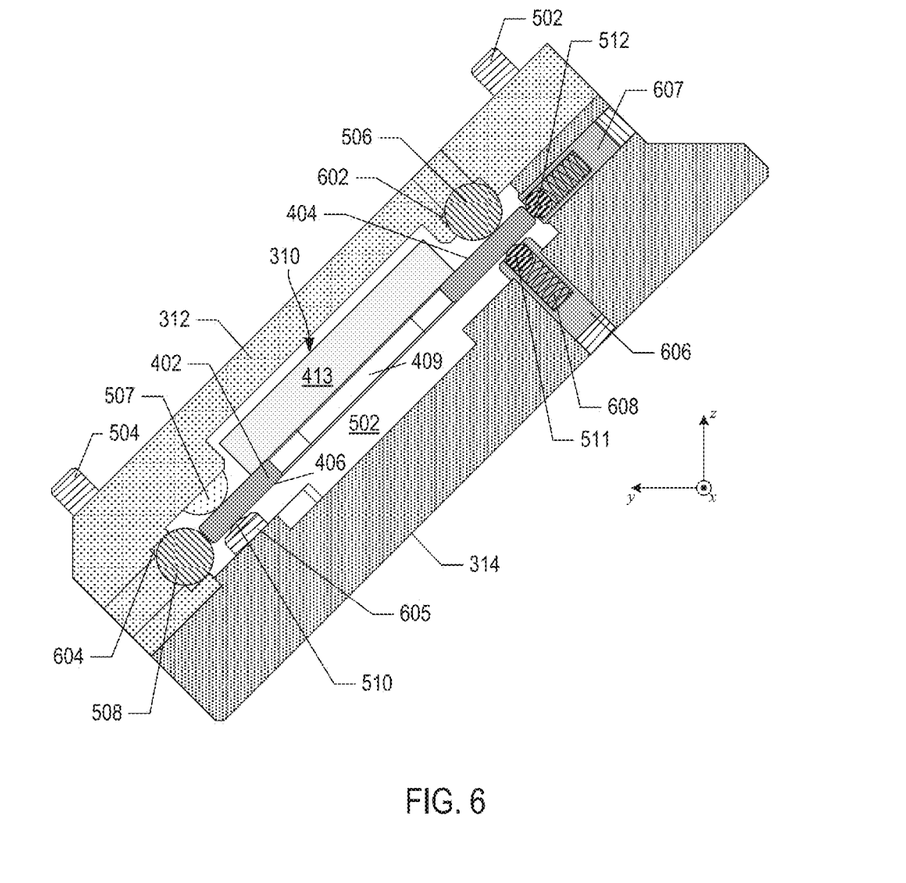
FIG. 6 shows a cross-sectional view of the supports and the polychroic-mirror array shown in FIG. 5.

FIG. 6 shows a cross-sectional view of the first and second supports 312 and 314 and the polychroic-mirror array 310. As shown in FIG. 6, the kinematic balls 506 and 508 sit in corresponding sockets 602 and 604 of the first support 312. The sliding elements 510-512 are also seated within spring loaded sockets of holders 605-607 that are inserted into openings of the second support 314. For example, the element 511 sits in a socket of the holder 606 and is pushed outward by a spring 608. Note that each kinematic ball seated in the first support 312 is located opposite a corresponding sliding element seated in the second support 314. The forces exerted by the springs against the sliding elements 510-512 force the surface 404 against the kinematic balls 506-508. For example, the spring loaded sliding elements 510 and 511 are pushed by corresponding springs against the second surface 406, which, in turn, force the first surface 404 against the kinematic balls 506 and 507. As a result, the array 310 is held in place in the yz-plane by the kinematic balls 506-508 and the sliding elements 510-512, and because the kinematic balls 506-508 are statically located within their corresponding sockets and the plate 400 can slide between the sliding elements 510-512 and the kinematic balls 506-508, the array 310 is held firmly in place between first and second supports 312 and 314 and can be moved smoothly back and forth within the opening 502 in the x-direction. In other words, as the first surface 404 of the plate 402 slides across the kinematic balls 506-508, the polychroic mirror reflective surfaces are maintained within a single plane throughout the entire sliding motion. As a result, co-alignment of the polychroic mirrors 412-415 can be maintained after repeated movement of the plate 402.

A specimen composed of many different components is deposited on a slide which is placed on the stage of the modular imaging system described above with reference to FIG. 1. Each type of component of the specimen can be labeled with a particular fluorescent probe. In other words, each type of probe is designed to bind specifically to a particular component of the specimen, and a different type of fluorophore is bound to a particular type of probe. As mentioned above, the beam 208 is composed of a number of separate, high-intensity, substantially monochromatic excitation channels. When the specimen is illuminated by the beam 208 each channel causes a type of fluorophore to emit light with a different channel in the visible portion of the electromagnetic spectrum. As a result, each component of the specimen can be displayed with a different associated channel or color. The different wavelengths of light emitted from the fluorophores are called "emission channels." Different subsets of components of the specimen can be illuminated by sliding a particular polychroic mirror of the array 310 into the path of the beam 208, as shown in FIG. 5. In other words, each polychroic mirror of the array 310 reflects a different subset of excitation channels of the beam 208 input to the excitation-channel selector 214 through the opening 212. The particular subset of excitation channels is selected by sliding the polychroic-mirror array 310 so that a polychroic mirror reflects the selected subset of excitation channels to the mirror 216 of the mirror support 218.

Figure 7:
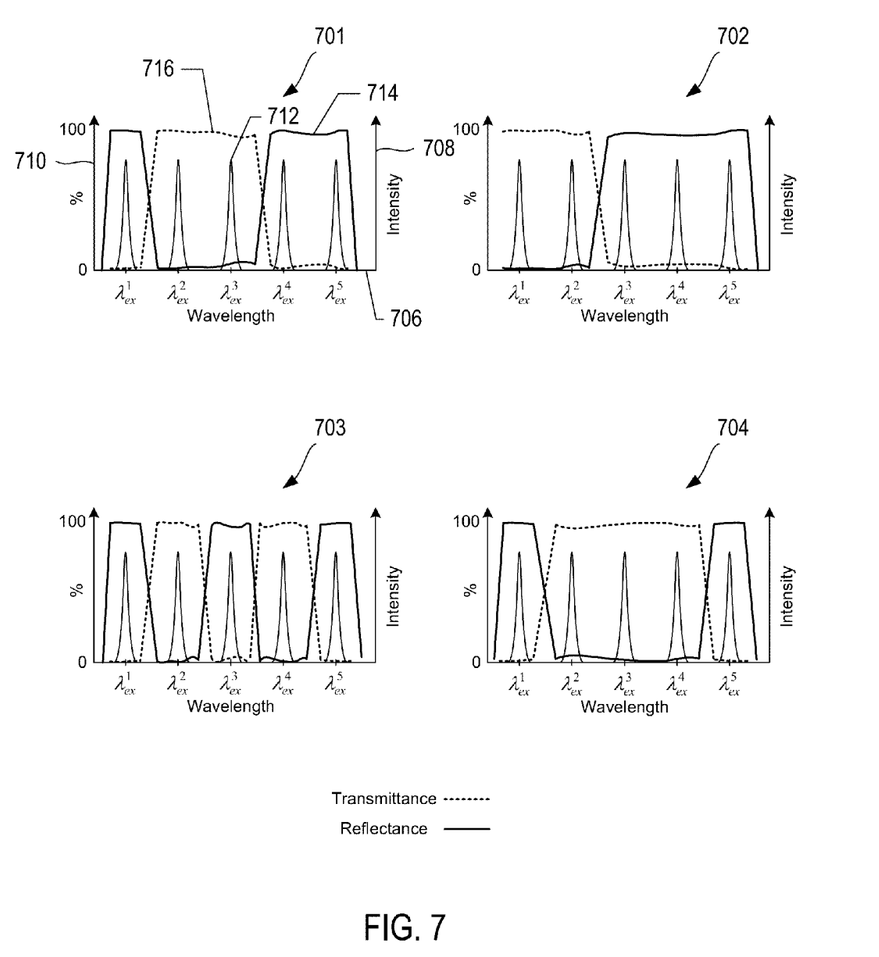
FIG. 7 shows example plots of excitation channels and transmittance and reflectance associated with polychroic mirrors of a polychroic-mirror array.

FIG. 7 shows example plots 701-704 of excitation channels of a beam of excitation light and transmittance and reflectance associated with the polychroic mirrors 412-415 of the array 310. Each plot includes a horizontal axis, such as horizontal axis 706, that represents wavelength, a first vertical axis, such as vertical axis 708, that represents intensity, and a second vertical axis, such as vertical axis 710, that represents percentage of reflectance and transmittance. In plots 701-704, each peak represents a very narrow range of wavelengths centered about a particular excitation channel. For example, peak 712 is centered about an excitation channel $\lambda_{ex}^3$. Solid-line curves, such as curve 714, represent reflectance; and dashed-line curves, such as curve 716, represent transmittance. Each polychroic mirror operates as a filter that reflects a subset of excitation channels while transmitting other excitation channels. For example, the plots 701-704 can represent the reflectance and transmittance of the polychroic mirrors 412-415, respectively. In plot 701, the mirror 412 reflects channels $\lambda_{ex}^1$, $\lambda_{ex}^4$, and $\lambda_{ex}^5$ and transmits channel $\lambda_{ex}^2$ and $\lambda_{ex}^3$. In plot 702, the mirror 413 reflects channels $\lambda_{ex}^3$, $\lambda_{ex}^4$, and $\lambda_{ex}^5$ and transmits channels $\lambda_{ex}^1$ and $\lambda_{ex}^2$. In plot 703, the mirror 414 reflects channels $\lambda_{ex}^1$, $\lambda_{ex}^3$, and $\lambda_{ex}^5$ and transmits channels $\lambda_{ex}^2$ and $\lambda_{ex}^4$. In plot 704, the mirror 415 reflects channels $\lambda_{ex}^1$ and $\lambda_{ex}^5$ and reflects channels $\lambda_{ex}^2$, $\lambda_{ex}^3$, and $\lambda_{ex}^4$.

Figure 8:
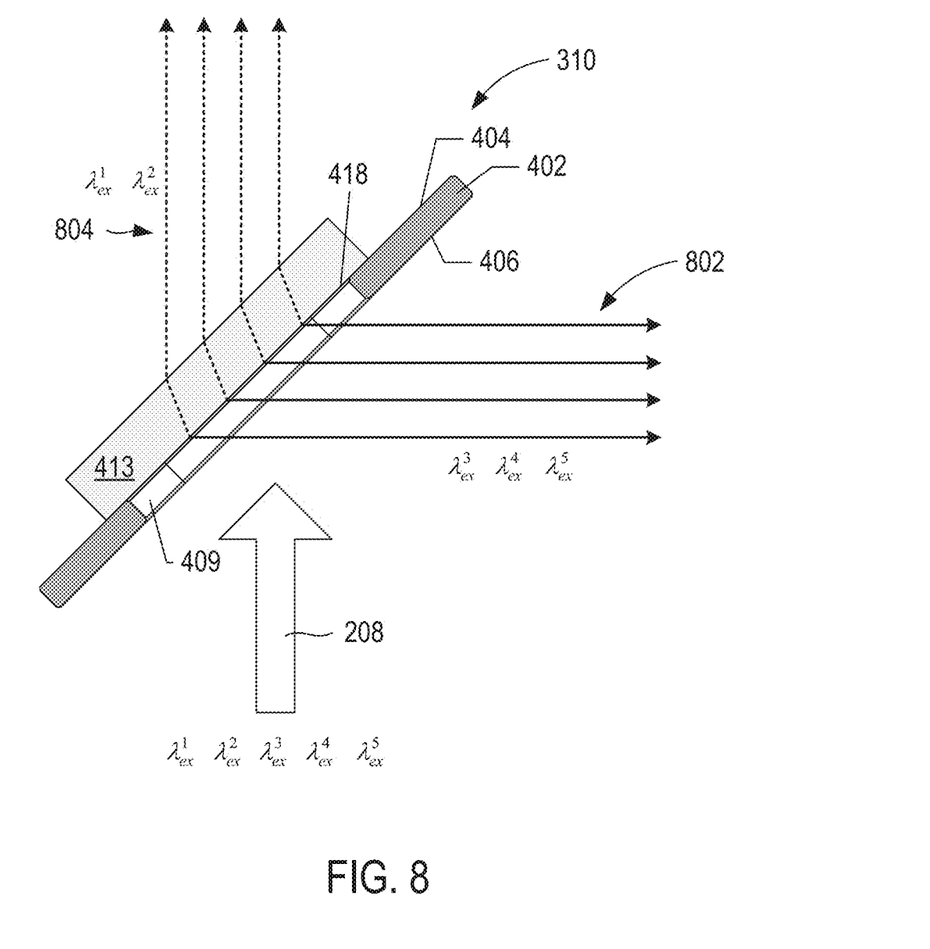
FIG. 8 shows a cross-sectional view of the polychroic-mirror array shown in FIG. 4C.

FIG. 8 shows a cross-sectional view of the array 310 shown in FIG. 4C. The reflective surface 802 of the polychroic mirror 413 is attached to the first surface 404 and is exposed through the hole 409. As shown in FIG. 8, the beam 208 is composed of the excitation channels $\lambda_{ex}^1$, $\lambda_{ex}^2$, $\lambda_{ex}^3$, $\lambda_{ex}^4$, and $\lambda_{ex}^5$, which strikes the reflective surface 802 of the mirror 413 through the hole 409. Dash-line directional arrows 804 represent transmitted excitation channels, and solid-line directional arrows 806 represent reflected excitation channels. As described above with reference to plot 702, the excitation channels $\lambda_{ex}^3$, $\lambda_{ex}^4$, and $\lambda_{ex}^5$ are reflected from the surface 418 as beam 802 that passes through the hole 409 and the excitation channels $\lambda_{ex}^1$ and $\lambda_{ex}^2$ are transmitted through the mirror 413 as beam 804.

Figure 9:
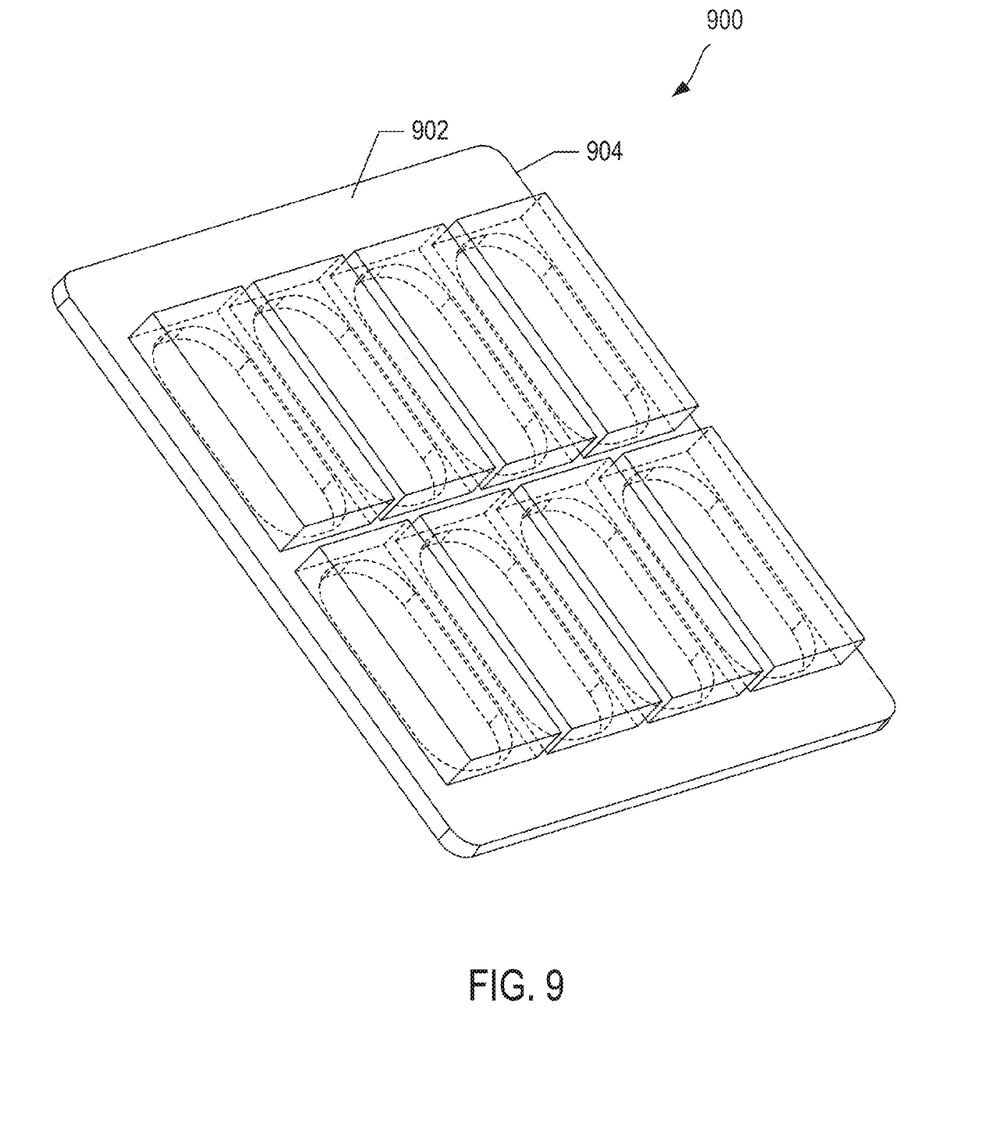
FIG. 9 shows an isometric view of a polychroic-mirror array plate with a two-dimensional array of polychroic mirrors.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. The examples are not intended to be exhaustive of or to limit this disclosure to the precise forms described. For example, polychroic-mirror arrays are not limited to a series of four polychroic mirrors. An array can be configured with any number of polychroic mirrors with a linear or one-dimensional arrangement. In addition, polychroic-mirror arrays can be configured with a two-dimensional array of polychroic mirrors as shown in FIG. 9. In FIG. 9, an array 900 is composed of two rows of polychroic mirrors with reflective surfaces attached to a first planar surface 902 of a plate 904. The reflective surfaces of the mirrors are exposed through corresponding holes, as described above with reference to FIG. 4. In other embodiments, the array is not limited to the first and second surfaces being parallel. The first and second surfaces can be non-parallel and the plate may not have a uniform thickness. In other embodiments, the first surface can be a highly polished planar surface as described above while the second surface is not. In still other embodiments, the first surface can be provided with one or more recesses in the regions of the plate surrounding the openings, e.g. by machining or etching, leaving two or more support sections in the plane of the first surface for supporting the polychroic mirrors to lie within the same plane that corresponds to the single plane of motion when adhered to the plate.

Obviously, many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated. It is intended that the scope of this disclosure be defined by the following claims and their equivalents:

The invention claimed is:

1. A microscopy system comprising:
   a light source arranged to emit a number of excitation channels;
   a polychroic-mirror changer having a first opening arranged to receive the excitation channels and a second opening; and
   a polychroic-mirror array positioned within the changer and arranged to intersect the excitation channels, wherein the array includes a planar arrangement of two or more polychroic mirrors, each polychroic mirror arranged to reflect a different subset of the excitation channels through the second opening and into an objective lens to illuminate a specimen when the polychroic-mirror changer and the array are moved in a single plane of motion.

2. The system of claim 1, wherein the polychroic-mirror array includes a plate with a planar first surface and a second surface located opposite the first surface and has a number of holes that extend from the first surface to the second surface.

3. The system of claim 1, wherein each polychroic mirror is attached to the first surface and covers a hole such that each polychroic mirror is to receive the excitation channels through a corresponding hole and is to reflect a set of excitation channels back through the hole.

4. The system of claim 1, wherein the first surface of the plate is wear resistant.

5. The system of claim 1, wherein the planar arrangement of polychroic mirrors is one-dimensional.

6. The system of claim 1, wherein the planar arrangement of polychroic mirrors is two-dimensional.

7. The system of claim 1, further comprising a motor connected to the array, wherein the motor is to incrementally move the array within the single plane of motion so that a polychroic mirror intersects the excitation channels.

8. The system of claim 1, wherein in the planar arrangement of polychroic mirrors lies within the single plane of motion.

9. A polychroic-mirror changer of a microscope comprising:
    a first support;
    a second support attached to the first support and having a first opening and a second opening; and
    a polychroic-mirror array, the array includes a planar arrangement of polychroic mirrors attached to a plate to be moved within a single plane of motion between the first and second supports, wherein each polychroic mirror is to receive excitation channels through the first opening and reflect a subset of the excitation channels through the second opening to illuminate a specimen through an objective lens.

10. The changer of claim 9, wherein the polychroic-mirror array includes a plate with a planar first surface and a planar second surface located opposite the first surface and has a number of holes that extend from the first surface to the second surface.

11. The changer of claim 9, wherein each polychroic mirror is attached to the first surface and covers a hole such that each polychroic mirror is to receive the excitation channels through a corresponding hole in the plate and is to reflect a subset of excitation channels back through the hole.

12. The changer of claim 9, wherein the first surface of the plate is wear resistant.

13. The changer of claim 9, wherein the planar arrangement of polychroic mirrors is one-dimensional.

14. The changer of claim 9, wherein the planar arrangement of polychroic mirrors is two-dimensional.

15. The changer of claim 9, further comprising a motor connected to the array, wherein the motor is to incrementally move the array within the single plane of motion so that a polychroic mirror intersects the excitation channels.

16. The changer of claim 9, wherein in the planar arrangement of polychroic mirrors lies within the single plane of motion.

17. The changer of claim 9, wherein the first support includes at least three kinematic balls disposed within sockets of the first support to form the single plane of motion and the second support includes at least three sliding elements that force the first surface of the plate against the kinematic balls.

18. The changer of claim 9, wherein each polychroic mirror is to reflect a different subset of the excitation channels.

19. The changer of claim 9, further comprises a mirror attached to the second support, the mirror to receive the subset of excitation light output through the second opening and reflect the subset through a third opening in the second support to the objective lens.

* * * * *